United States Patent

Wake et al.

[11] Patent Number: 6,044,288
[45] Date of Patent: Mar. 28, 2000

[54] APPARATUS AND METHOD FOR DETERMINING THE PERIMETER OF THE SURFACE OF AN OBJECT BEING SCANNED

[75] Inventors: Robert H. Wake, Sunrise; Richard J. Grable, Plantation, both of Fla.; David P. Rohler, University Heights, Ohio

[73] Assignee: Imaging Diagnostics Systems, Inc., Plantation, Fla.

[21] Appl. No.: 08/965,148

[22] Filed: Nov. 6, 1997

Related U.S. Application Data

[60] Provisional application No. 60/029,897, Nov. 8, 1996, and provisional application No. 60/029,898, Nov. 8, 1996.

[51] Int. Cl.[7] .......................................... A61B 5/00
[52] U.S. Cl. ...................... 600/407; 600/476; 600/587; 250/236; 356/376
[58] Field of Search ................................. 356/376, 379, 356/383, 384, 388, 387; 329/196, 223, 226, 205, 212, 216, 225; 250/234–236; 600/407, 473, 476, 587

[56] References Cited

U.S. PATENT DOCUMENTS

| | | |
|---|---|---|
| 4,500,784 | 2/1985 | Hacskaylo . |
| 5,148,022 | 9/1992 | Kawaguchi et al. . |
| 5,353,799 | 10/1994 | Chance . |
| 5,376,796 | 12/1994 | Chan et al. . |
| 5,384,573 | 1/1995 | Turpin . |
| 5,386,447 | 1/1995 | Siczek . |
| 5,409,497 | 4/1995 | Siczek et al. . |
| 5,411,024 | 5/1995 | Thomas et al. . |
| 5,426,685 | 6/1995 | Pellegrino et al. . |
| 5,432,703 | 7/1995 | Clynch et al. . |
| 5,439,000 | 8/1995 | Gunderson et al. . |
| 5,471,541 | 11/1995 | Burtnyk et al. . |
| 5,477,051 | 12/1995 | Tsuchiya . |
| 5,477,371 | 12/1995 | Shafir . |
| 5,506,683 | 4/1996 | Yang et al. . |
| 5,530,652 | 6/1996 | Croyle et al. . |
| 5,555,885 | 9/1996 | Chance . |
| 5,636,030 | 6/1997 | Limbach ................................. 356/376 |

*Primary Examiner*—Ruth S. Smith
*Attorney, Agent, or Firm*—Shlesinger, Arkwright & Garvey LLP

[57] ABSTRACT

An apparatus for determining the perimeter of an object being scanned comprises a scanning chamber for receiving therein an object being scanned; a source of laser beam disposed within the scanning chamber for impinging on the object being scanned, the laser beam being adapted to orbit around the object; an array of sensors disposed within the chamber, each of the sensors being adapted to detect light emanating from the surface of the object due to the laser beam exiting from the object; and each of the sensors being disposed such that at least only one of the sensors generates a peak response to light emanating from a point on the surface at a predetermined distance from a reference point, such that at each angular position of the laser beam in the orbit, a specific point at a distance from the reference is determined, thereby to generate a set of points representing the perimeter of the surface after a complete orbit.

19 Claims, 7 Drawing Sheets

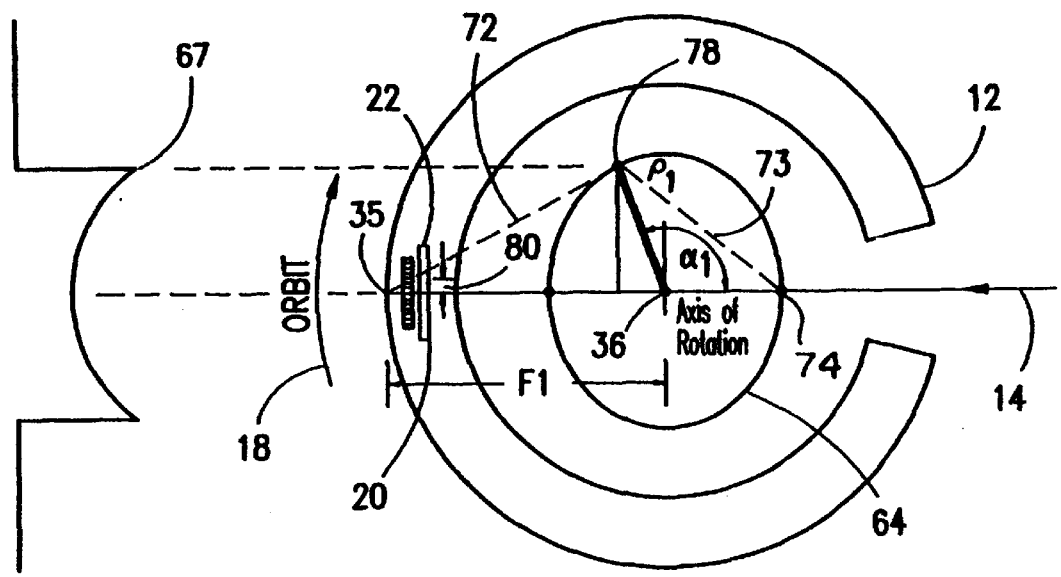
FIG. 7B    FIG. 7A
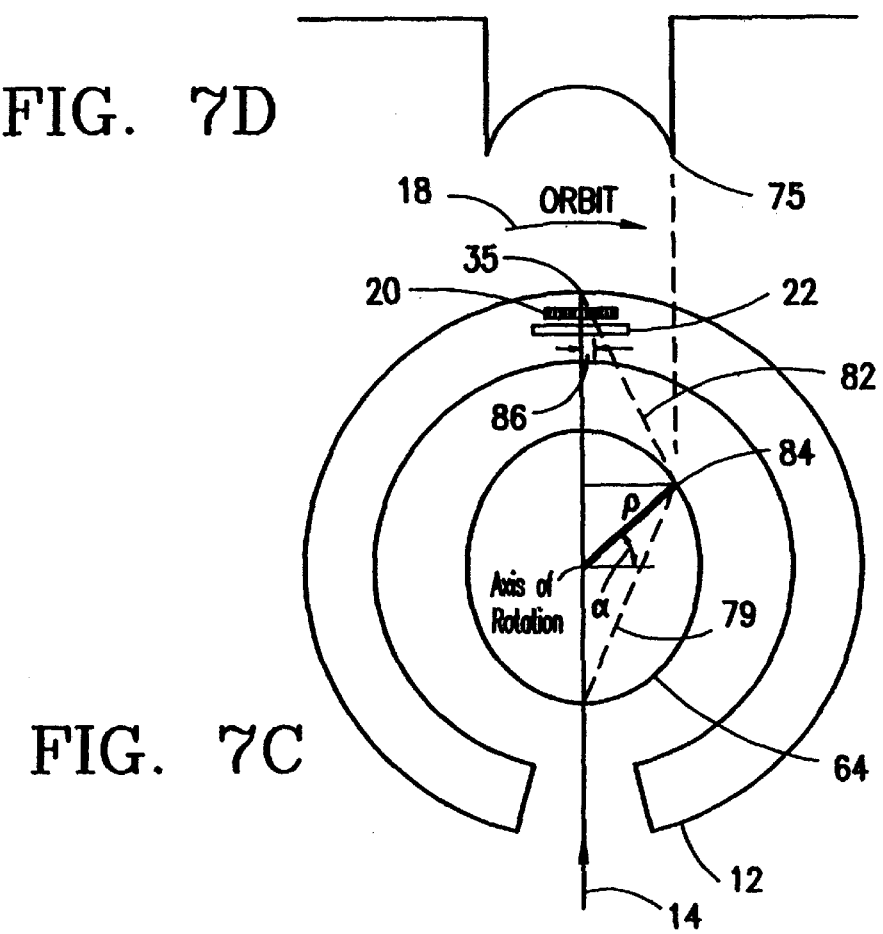
FIG. 7D
FIG. 7C

FIG. 12
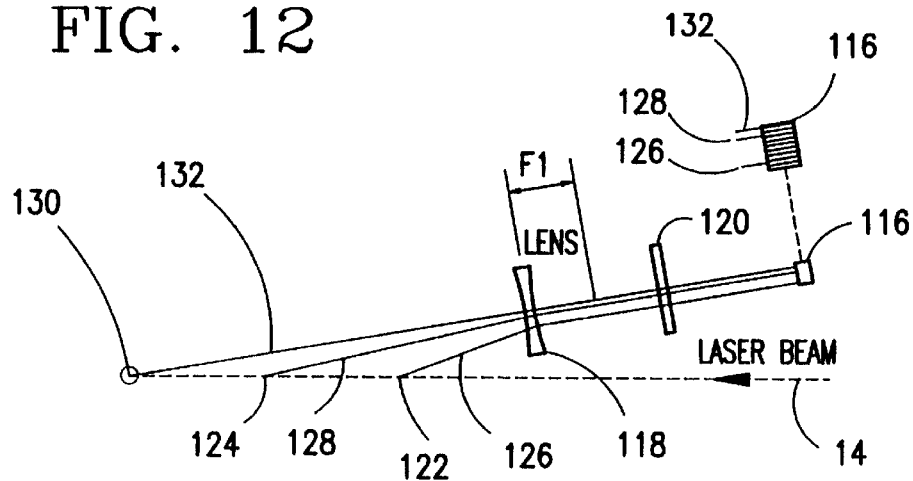
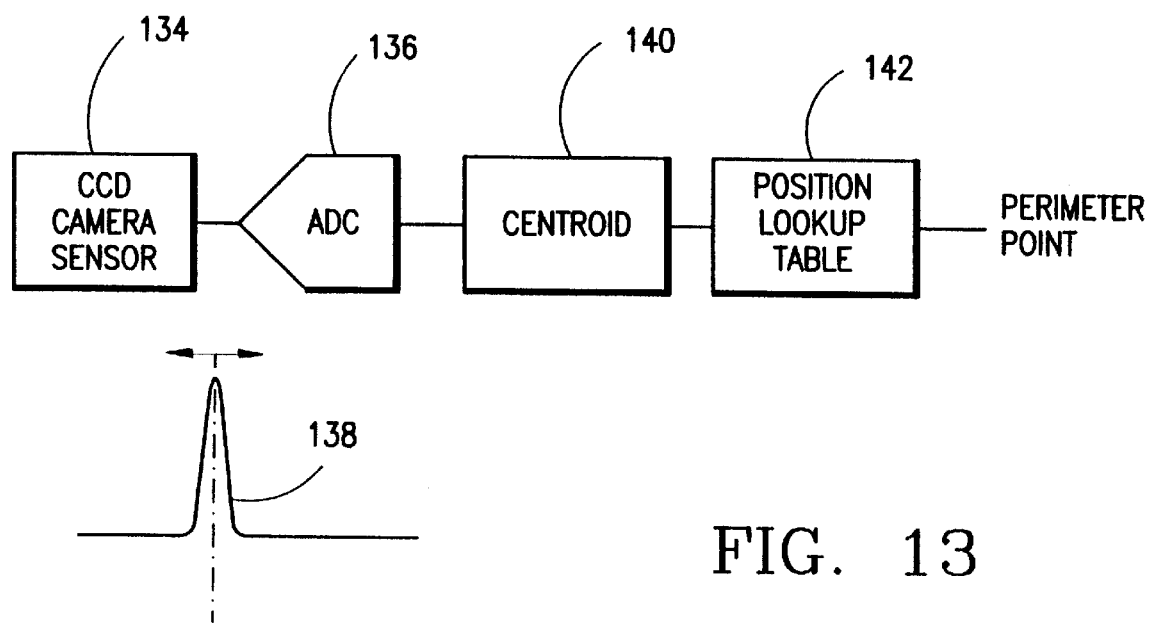
FIG. 13

APPARATUS AND METHOD FOR DETERMINING THE PERIMETER OF THE SURFACE OF AN OBJECT BEING SCANNED

RELATED APPLICATIONS

This application claims the priority benefit of Provisional Application Ser. No. 60/029,897, filed on Nov. 8, 1996, and is related to Provisional Application Ser. No. 60/029,898, filed on Nov. 8, 1996, both of which are hereby incorporated by reference.

This application is also related to copending application Ser. No. 08/484,904, filed Jun. 7, 1995, now U.S. Pat. No. 5,692,511, issued on Dec. 2, 1997, which is hereby incorporated by reference.

FIELD OF THE INVENTION

The present invention relates generally to a diagnostic medical imaging apparatus that employs a near-infrared laser as a radiation source and more particularly to a device for use in the imaging apparatus for determining the perimeter of the surface of the object or tissue being scanned.

BACKGROUND OF THE INVENTION

Cancer of the breast is a major cause of death among the American female population. Effective treatment of this disease is most readily accomplished following early detection of malignant tumors. Major efforts are presently underway to provide mass screening of the population for symptoms of breast tumors. Such screening efforts will require sophisticates, automated equipment to reliably accomplish the detection process.

The x-ray absorption density resolution of present photographic x-ray methods is insufficient to provide reliable early detection of malignant tumors. Research has indicated that the probability of metastasis increases sharply for breast tumors over 1 cm in size. Tumors of this size rarely produce sufficient contrast in a mammogram to be detectable. To produce detectable contrast in photographic mammogram 2–3 cm dimensions are required. Calcium deposits used for inferential detection of tumors in conventional mammography also appear to be associated with tumors of large size. For these reasons, photographic mammography has been relatively ineffective in the detection of this condition.

Most mammographic apparatus in use today in clinics and hospitals require breast compression techniques which are uncomfortable at best and in many cases painful to the patient. In addition, x-rays constitute ionizing radiation which injects a further risk factor into the use of mammographic techniques as most universally employed.

Ultrasound has also been suggested as in U.S. Pat. No. 4,075,883, which requires that the breast be immersed in a fluid-filled scanning chamber U.S. Pat. No. 3,973,126 also requires that the breast be immersed in a fluid-filled chamber for an x-ray scanning technique.

In recent times, the use of light and more specifically laser light to non-invasively peer inside the body to reveal the interior structure has been investigated. This techniques is called optical imaging. Optical imaging and spectroscopy are key components of optical tomography. Rapid progress over the past decade have brought optical tomography to the brink of clinical usefulness. Optical wavelength photons do not penetrate in vivo tissue is a straight line as do x-ray photons. This phenomena causes the light photons to scatter inside the tissue before the photons emerge out of the scanned sample.

In optical tomography, mathematical formulas and projections techniques have been devised to perform a reconstruction function somewhat similar to x-ray tomography. However, because light photon propagation is not a straight line, techniques to produce cross-section images are mathematically intensive and invariably require establishing the boundary of the scanned object. Boundary determination is important because it serves as the basis for reconstruction techniques to produce interior structure details. Algorithms to date do not use any form of direct measurement techniques to establish the boundary of the scanned object.

OBJECTS AND SUMMARY OF THE INVENTION

It is an object of the present invention to provide a direct determination of the boundary of the scanned object by sensing the light exiting from the scanned object from a specific location that is fixed in relation to the impinging laser beam.

It is another object of the present invention to provide a direct determination of the boundary of the scanned object with a linear array of detectors that is calibrated to a specific angle of a light ray emerging from the scanned object.

It is still another object of the present invention to provide a direct determination of the boundary of the scanned object that can be used to determine the optical path length of a laser beam through the scanned object for use in reconstructing an image of the scanned object.

In summary, the present invention provides an apparatus for determining the perimeter of an object being scanned comprising a scanning chamber for receiving therein an object being scanned; a source of laser beam disposed within the scanning chamber for impinging on the object being scanned, the laser beam being adapted to orbit around the object; an array of sensors disposed within the chamber, each of the sensors being adapted to detect light emanating from the surface of the object due to the laser beam exiting from the object; and each of the sensors being disposed such that at least only one of the sensors generates a peak response to light emanating from a point on the surface at a predetermined distance from a reference point, such that at each angular position of the laser beam in the orbit, a specific point at a distance from the reference is determined, thereby to generate a set of points representing the perimeter of the surface after a complete orbit.

The present invention also provides a method for determining the perimeter of an object being scanned, comprising the steps of providing a source of laser beam; directing the laser beam toward the object being scanned; orbiting the laser beam around the object; providing a plurality of sensors adapted to detect light emanating from the surface after due to the laser beam exiting from the object; and detecting at each angular position of the orbit light emanating from the surface of the object at a unique one of the sensors for each point on the surface at a predetermined specific distance from a reference point such that a collection of points from the surface are generated during a complete orbit of the laser beam.

These and other objects of the present invention will become apparent from the following detailed description.

BRIEF DESCRIPTIONS OF THE DRAWINGS

FIGS. 7A, 7B, 7C and 7D show the generation of a perimeter plot of a scanned object of unknown size.

FIG. 12 is an enlarged view of a portion of FIG. 10, showing in greater detail the reflected rays and the selected elements of the sensor array that are illuminated by the rays.

FIG. 13 is a schematic block diagram of a circuit for determining the perimeter locations from the output of the sensor used in FIG. 11.

DETAILED DESCRIPTION OF THE INVENTION

Figure 1:
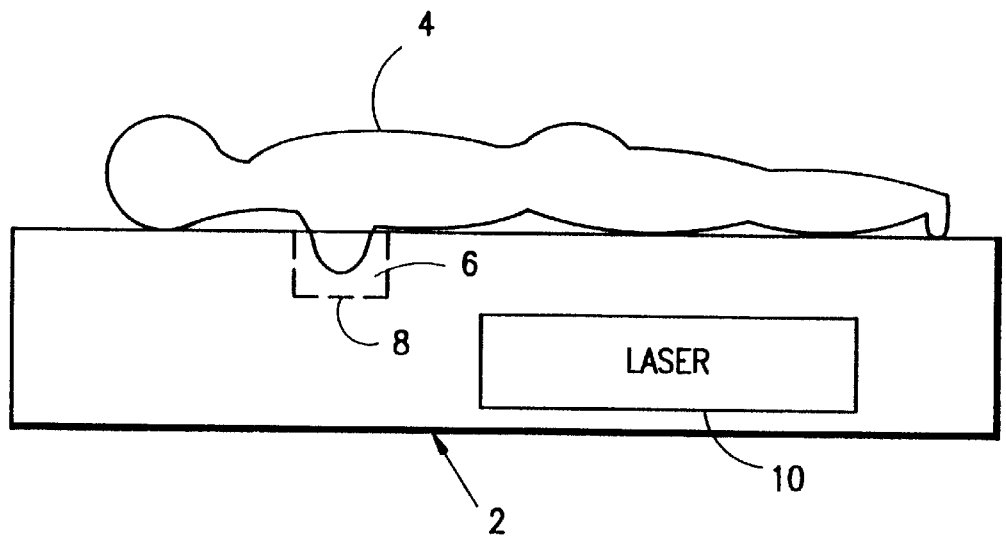
FIG. 1 is a schematic side elevational view of a scanning apparatus including a scanning chamber made in accordance with the present invention, showing a patient positioned on a support platform with her breast pendent within the scanning chamber for optical tomographic study.

A scanning apparatus 2, such as that described in copending application Ser. No. 08/484,904, filed Jun. 7, 1995, now U.S. Pat. No. 5,692,511, issued on Dec. 2, 1997, is schematically disclosed in FIG. 1. A patient 4 is positioned prone on a top surface of the apparatus 2 with her breast 6 pendent within a scanning chamber 8. A laser beam from a laser source 10 is operably associated with the scanning chamber 8 to illuminate the breast 6.

Figures 2A, 2B:
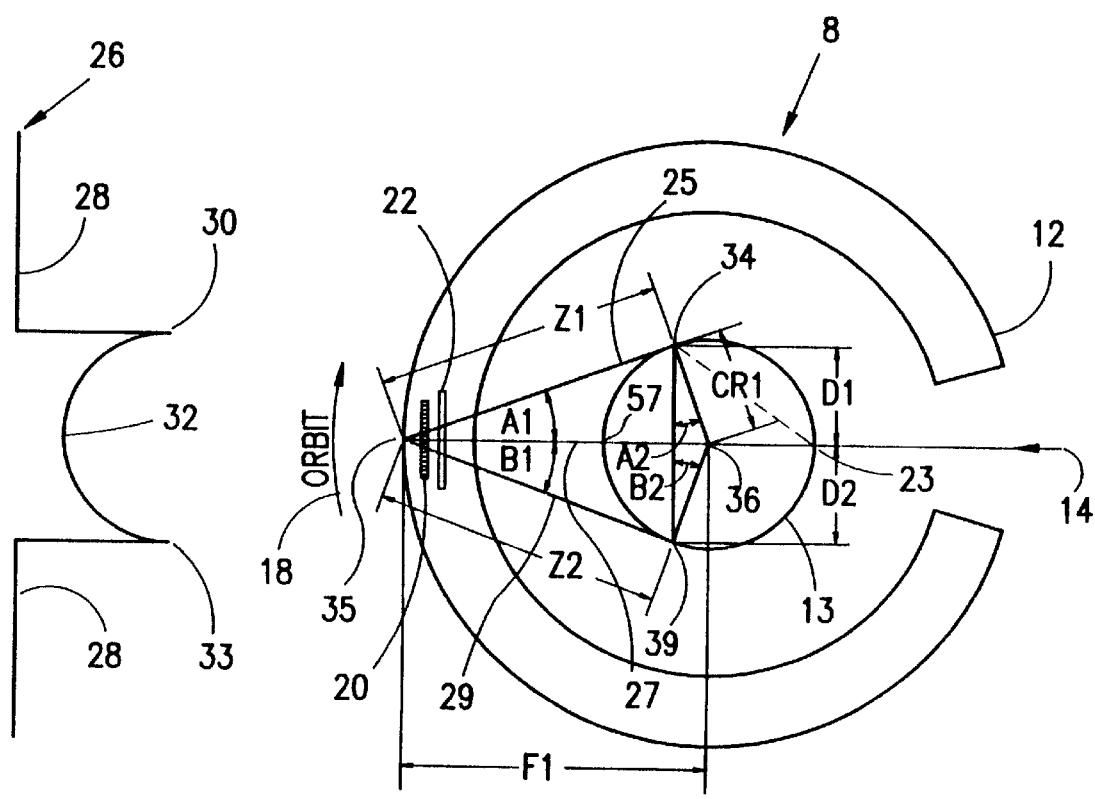
FIG. 2A is a schematic top view of the scanning chamber of FIG. 1, illustrating the geometrical relationships between a sensor array, sensor optics, tangent projection rays and impinging laser beam for a single diameter for scanned object.
FIG. 2B is a response curve of the sensor array of FIG. 2A used in determining the perimeter of the scanned object.

Referring to FIG. 2A, the scanning chamber 8 comprises of an array of detectors 12 disposed in an arc around an object to be scanned, such as a calibration standard 13. A laser beam 14 is brought into the scanning chamber to impinge on the object 13. A laser beam traversing through the breast 6 and exiting at any point will be picked up by one of the detectors in the array 12. The laser beam 14 and the array of detectors 12 are moved digitally in an orbit 18 around the object 13 at equally spaced angular positions until a complete circle has been traversed. At each angular position, light detected by the array of detectors 12 is recorded for later use in reconstructing an image of the object 13.

The scanning chamber 8 is provided with set of optical sensors 20 and optics 22 in accordance with the present invention to determine the perimeter of the object being scanned. The sensors 20 and optics 22 are disposed behind the detectors 12 and are also orbited around the object 13, along with the detectors 12 and the laser beam 14.

The optical sensors 20 and the associated optics 22 are positioned such that the laser beam impinging at point 23 will stimulate the sensors 20 as the beam exits along paths 25, 27 and 29 to produce a response curve 26, as best shown in FIG. 2B. The curve 26 has a low level region 28, a sharp edge or peak 30, a decreased light intensity region 32, another sharp edge 33 and another low level region 28. The low level regions 28 represent the response of the sensors 20 to ambient light inside the scanning chamber. The sharp edge 30 is generated by a light ray along the path 25 exiting from a point 34, which is tangent to the object 13 from a focal point 35 of the optics 22 at one point in the orbit of the scanning apparatus. The decreased light intensity region 32 is generated by a light ray along the path 27, exiting the object at point 37 and striking the sensors 20. The other sharp edge 33 is generated by a light ray along the path 29 exiting from a point 39, which is tangent to the object 13 from the focal point 35.

The laser beam 14 impinges on the calibration standard 13 at point 23. The distance F1 is selected to extend to the focal point 35 behind the sensors 20 to assure that the rays extending from the tangent point on the largest scanned object passed through the optics 22 and strike the sensors 20. The tangent point on the scanned object 13 is generally indicated at point 34. The path length 23–34, shown in dashed line, provides the shortest optical attenuation distance, and thus the highest signal 30 in the response curve 26, as best shown in FIG. 2B. The path length between points 23–37 provides the greatest optical attenuation distance and thus the lowest signal 32 in the response curve 26.

The sensors 20 are calibrated with objects of known diameters so that the peaks 30 and 33 of the signal 26 can be electronically decoded to plot the coordinates of the perimeter of the scanned object as the laser beam 14, the detector array 12, the sensors 20 and the optics 22 are orbited around the object being scanned.

Figures 3A, 3B:
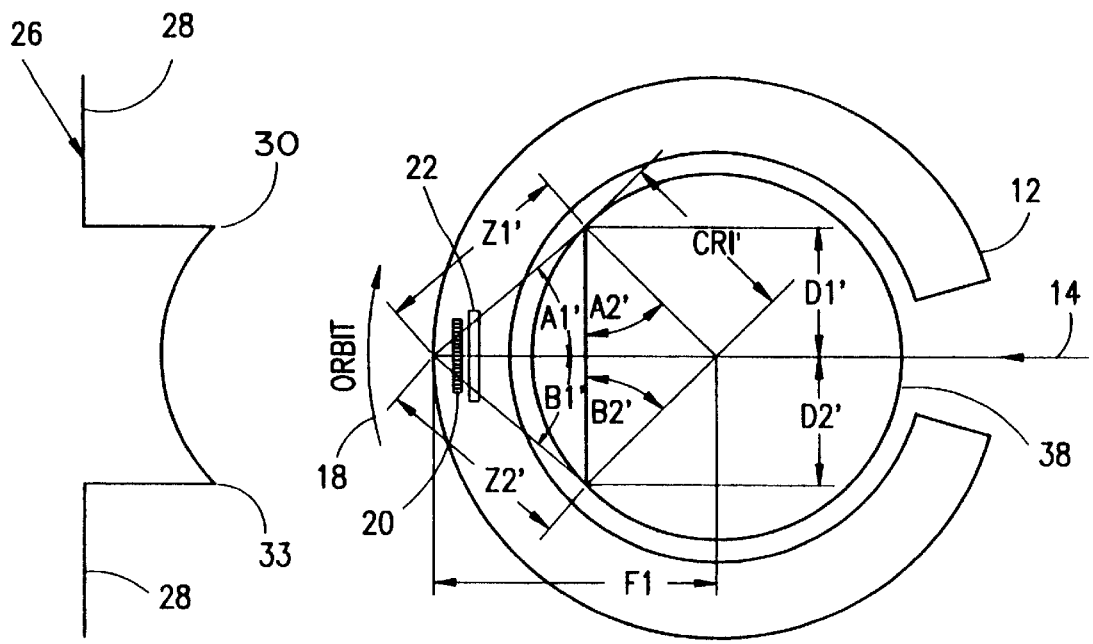
FIGS. 3A and 3B are similar to FIGS. 2A and 2B, showing a larger single diameter scanned object.

Calibration standards 13 and 38 with known diameters, one smaller corresponding to the smallest diameter that would be scanned, and the other larger representing the maximum diameter expected to be scanned, are used to calibrate the sensors 20, as best shown in FIGS. 2A and 3A. The system is orbited about an axis 36, which is a known point. Distance F1 is fixed by a mechanical design of the systems and is a known quantity. Distance CR1 is fixed as ½ of the diameter of the calibration standard 13. Angle A1 is determined from the following equation, $$A1 = \text{Arcsin}(CR1/F1) \quad (1)$$

Angle A1 equals A2 from geometry. Distance D1 is determined from the following equation, $$D1 = CR1 * \cos A2 \quad (2)$$

The same derivation can be used to determine the angle B1 and the distance D2 for the opposite side of the calibration standard 13.

Referring to FIG. 3A, the distance F1 is known, fixed by the mechanical design of the system. The distance CR1' is ½ of the diameter of the calibration standard 38. The angle A1' is determined from the following equation, $$A1' = \text{Arcsin}(CR1'/F1) \quad (3)$$

From geometry, angle A1' equals angle A2'. The distance D1' is calculated from the equation, $$D1' = CR1' * \cos A2' \quad (4)$$

The same derivation can be used to determine angle B1' and the distance D2' for the opposite side of the calibration standard 38.

The sensors 20 will generate a similar response curve 26 with peaks 30 and 33 further apart than with the smaller diameter object 13.

Each distance D1 as it varies from the smallest to the largest that can be detected by the sensors 20 and will provide a peak response from different sensors. By scanning several calibration standards, from the smallest to the largest that the scanning chamber is designed to accommodate, the response curve can be electronically decoded to plot the coordinate of the perimeter of the objects being scanned as the laser beam 14, the detector array 12, the sensors 20 and the sensor optics 22 are orbited around the scanned object in the direction 18.

Figures 4A, 4B:
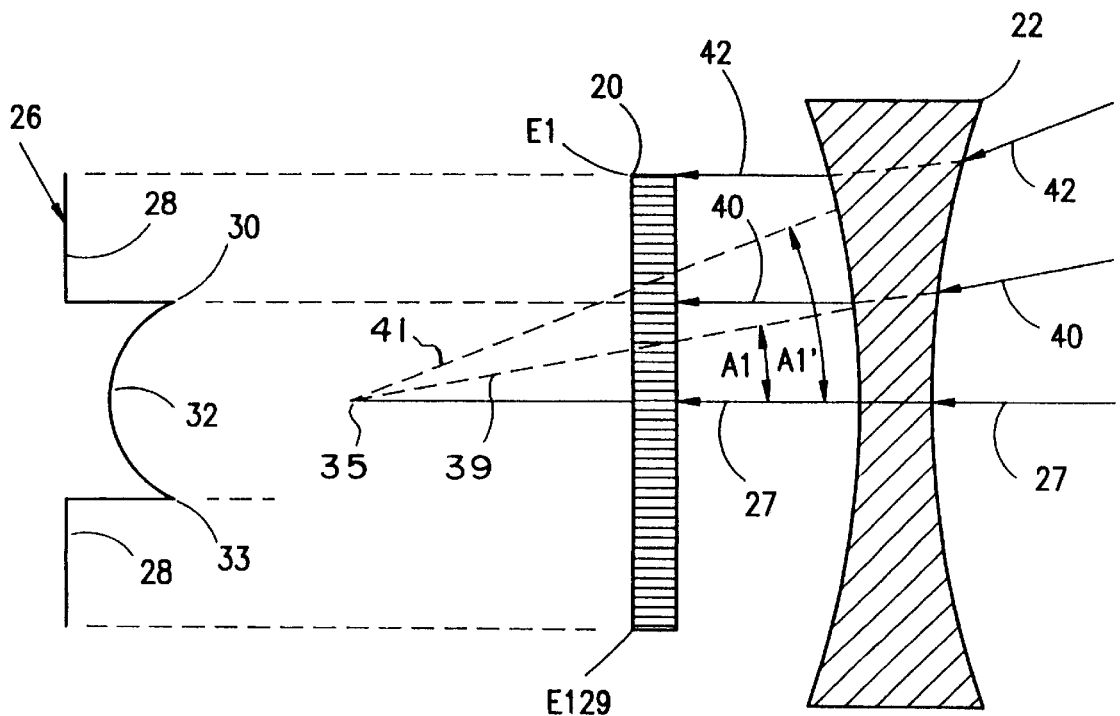
FIGS. 4A and 4B are enlarged views of the sensor array and the associated optics showing the exclusive relationship between the angles at which the rays impinge on the lens and are directed to specific elements of the sensor array.

The optical sensors 20 and the optics 22 are shown in greater detail in FIG. 4A. The sensors 20 are a linear array of contiguous detectors. In the present invention 128 detectors are used, although a different number may be used. Each detector resides at a specific physical location in the array, for example, E1 being the first detector and E1 29 being the last. The array is designed such that each element in the array can be examined and the signal level at its respective physical location can be measured. The optics 22, which is disclosed as a diverging lens, is designed to focus rays 40 and 42 onto the detector array. The ray 40 is a tangent ray from a smaller calibration diameter and will strike the detector array at a different element than the ray 42 which is a tangent ray from a larger calibration diameter. The ray 40 will generate a response curve similar to the curve 26, as best shown in FIG. 4B. The ray 42 will also generate a response curve similar to the curve 26. Each ray, since it is coming from a different distance D or D1', or angle A1 or A1', will intercept a unique array element. Therefore, each distance D1 or angle A1 can be calibrated to a unique element in the detector array 20, where each detector location is uniquely defined from a reference point, such as the detector that is stimulated by the ray 27 passing through the center of orbit of scanned object.

The angles A1 and A1' at which the rays are impinging on the lens 22 form exclusive relationships with specific elements of the sensor array 20. Since the focal point 35 of the lens 22 is a known distance from the axis of rotation 36, rays 40 and 42 emerging from the scanned objects 13 and 38 form specific angles A1 and A1' with respect to the axis of the laser beam 14, with the vertex of the angles at the focal point 35 of the lens 22. The broken lines 39 and 41 show the extension of the rays 40 and 42 in the absence of the lens 22. Simple reverse tracing of the rays 40 and 42 indicate that a specific element of sensor array 20 is illuminated by a respective ray of a specific angle with respect to the axis of the laser beam 14. This relationship allows perimeter detection with a peak detector configured as a leading edge pick off circuit to sense the sharp edge 30 of the response curve 26. Similarly a trailing edge pick off circuit could be configured to sense the sharp edge 33 on the opposite side of the scanned object.

Figure 5:
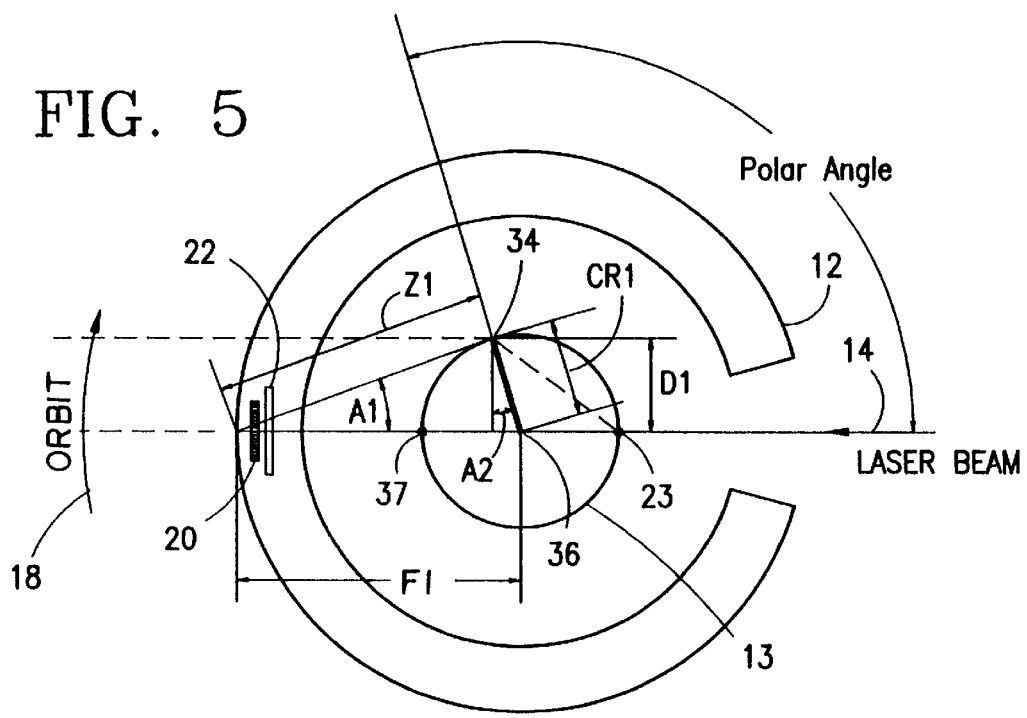
FIG. 5 shows the relationship of angle A1 and distance D1 to polar coordinates.
Figure 6:
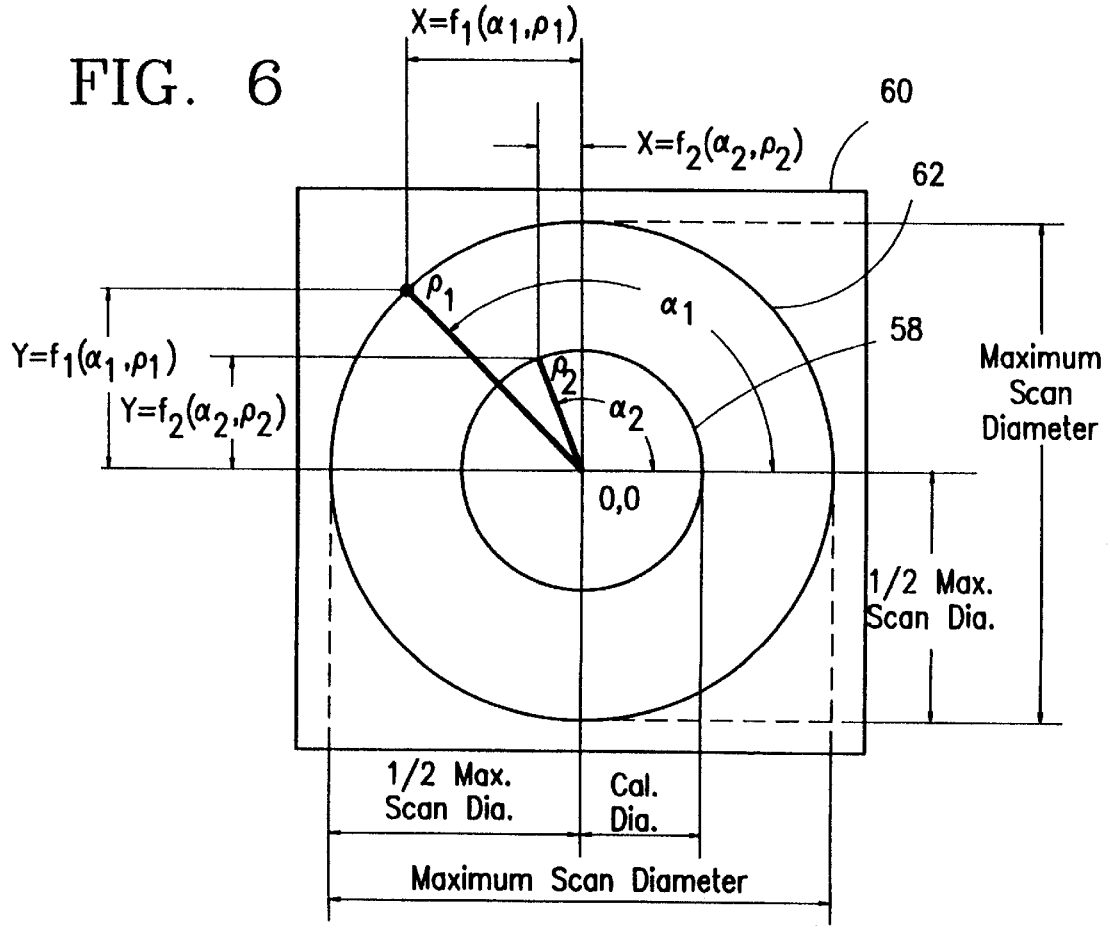
FIG. 6 is a matrix showing a plot of the perimeter of two scanned objects of constant diameters.

Referring to FIGS. 5 and 6, for each angle A1 and distance D1, a polar angle $\alpha$ and polar radius $\rho$ can be determined. The polar angle $\alpha$ is related to the angle A1 in the following equation, $$\text{Polar angle } \alpha = 180° - (90° - \text{angle } A1) \quad (5)$$

The polar radius $\rho$ is a function of angle A2 and the distance D1 as described by the following formula, $$\text{Polar radius } \rho = D1/\cos A2 \quad (6)$$

By computing the polar radius $\rho$ and the polar angle a at each point in the orbit of the laser beam 14, sensors 20 and optics 22 around the scanned object, a set of polar coordinate values can be obtained. When plotted on a polar coordinate matrix, the perimeter of the calibration object is mapped into a perimeter matrix. By using a calibration standard of known diameter, the units of the polar coordinate graph are defined. For example, if the calibration diameter of the scanned object is 4", the polar radius $\rho$ may be scaled to 2".

Another method of plotting the perimeter of the scanned object in a calibrated matrix would be to utilize the polar angle $\alpha$ and the distance D1 to directly identify a unique point in the matrix.

A larger calibration standard 38 of a known diameter, for example, the maximum scanned diameter of the apparatus, may be scanned to improve the accuracy of the calibration of the matrix, wherein the scale of the perimeter matrix could be verified by comparing the scale diameters with the actual diameters.

Referring to FIG. 6, the perimeter plot 58 corresponds to the calibration standard 13. The perimeter plot 62 corresponds to the calibration standard 38. The polar angle $\alpha$ and the polar radius $\rho$ specify a point (x,y) in a x, y perimeter matrix 60. For example, a point in the perimeter specified by polar angle $\alpha 1$ and polar radius $\rho$ is also defined by point $X1=F(\alpha 1, \rho\, 1), Y1=F(\alpha 1, \rho\, 1)$. Similarly, for a point defined by polar angle $\alpha 2$ and polar radius $\rho\, 2$, the same point is specified by $X2=F(\alpha 2, \rho\, 2)$, and $Y2=F(\alpha 2, \rho\, 2)$. The matrix 60 has been scaled to the actual physical dimensions of the calibration standards.

Figure 8:
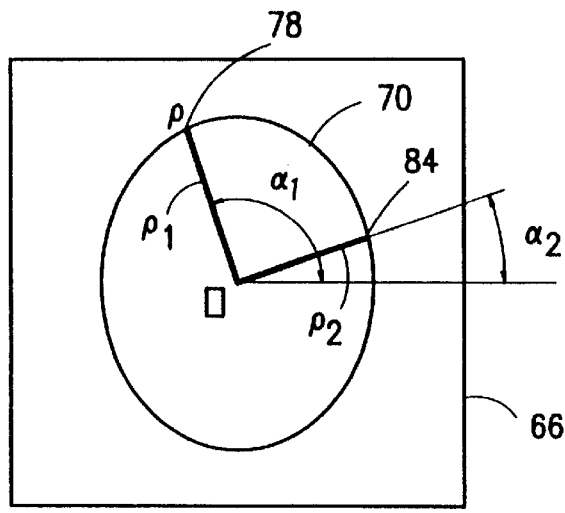
FIG. 8 is perimeter plot of the scanned object shown in FIGS. 7A, 7B, 7C and 7D.

Referring to FIG. 7A, a non-cylindrical object 64 is scanned at one orbit position. At the starting point (0°) of the orbit a ray 72 drawn from the focal point 35 on the distance F1 from the axis of rotation 36 to a tangent point 78 on the object 64 passes through the array 20 and is seen in a detector at distance 80. The ray 72 generates a peak 67, as best shown in FIG. 7B, since the light would have traveled the least distance 73 within the object. From the look-up table for the distance 80 on the array, the polar radius $\rho\, 1$ and the polar angle $\alpha 1$ are determined for the scan angle 0°. In FIG. 7C, after some number of degrees of rotation in the orbit, for example 90°, the laser beam 14 impinges on the object 64. A ray 82 drawn from the point 35 to a tangent point 84 on the object 64 passes through array 20 and is seen in a detector at a distance 86 on the array. The ray 82 generates a peak 75, as best shown in FIG. 7D, since the light would have traveled the least distance 79 within the object. From the look-up table for the distance 86 on the array, the polar radius $\rho\, 2$ and the polar angle $\alpha 2$ are determined for the scan angle 90°. The perimeter points 78 and 84 from the scanned object thus obtained are plotted onto the perimeter matrix 66, as best shown in FIG. 8. For angles between 0° and 359°, the process of determining the polar angle $\alpha$, measuring the distance on the array 20, determining the polar radius $\rho$ from the look-up table and identifying the point in the perimeter matrix is repeated. Through this process, the perimeter of the object 64 is mapped into the perimeter matrix.

Figure 9:
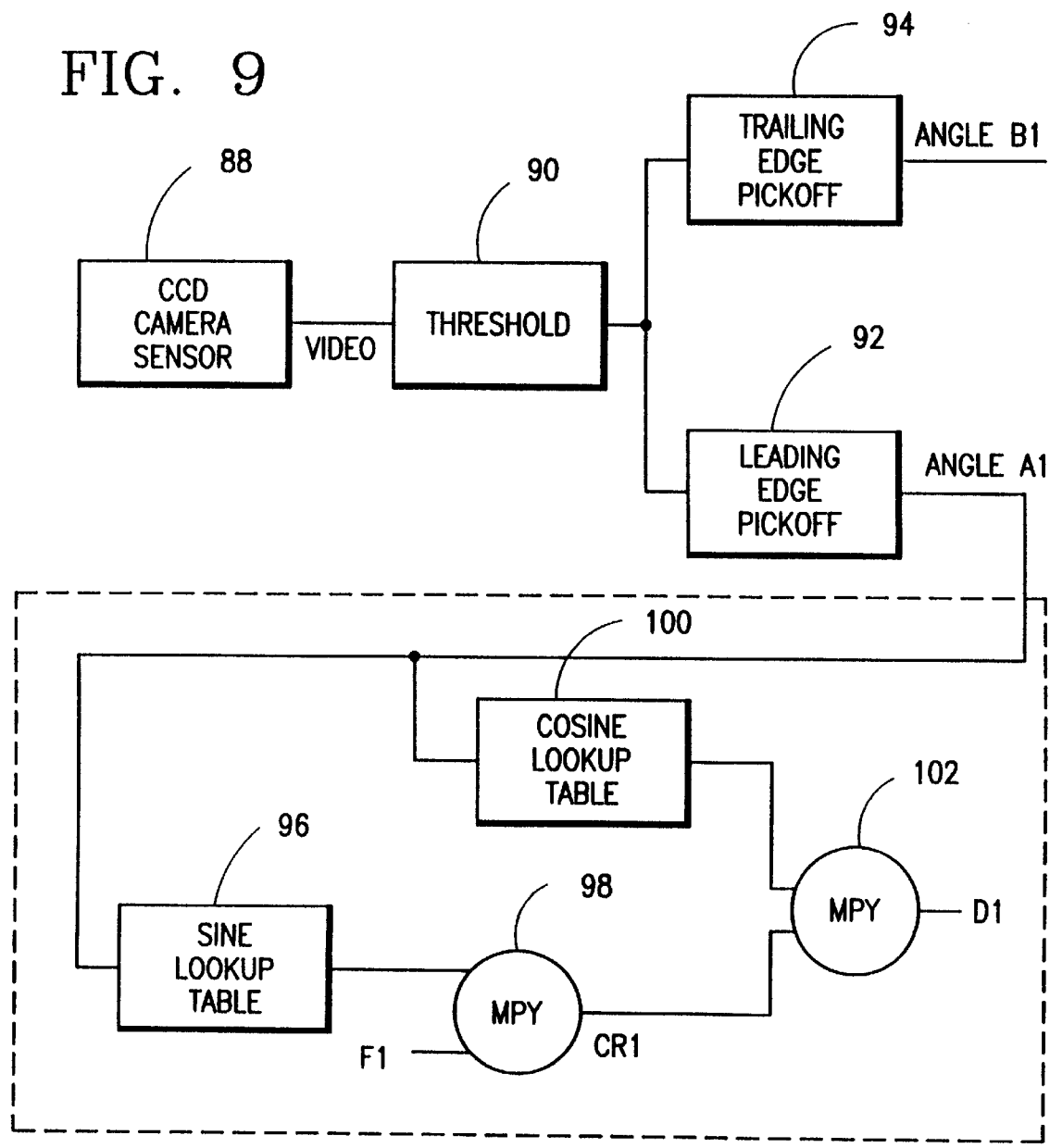
FIG. 9 is a schematic block diagram of a circuit for determining the perimeter data from the scanned object from the output of the sensor array.

An exemplary circuit for perimeter detection is disclosed in FIG. 9. The sensors 20 may be implemented by a linear 1-dimensional ccd (charge coupled device) sensor 88, which is a television pick up device supplied by Texas Instruments, EG&G and others. The ccd sensor 88 outputs an analog video signal corresponding to the light received by the sensor. The video signal corresponds to the response curve 26. The video signal is thresholded at circuit block 90 to determine the sharp edges 30. The leading edge is angle A1 and the trailing edge is angle B1. The leading edge is picked off at circuit block 92 and the trailing edge at 94. The processing of each is identical and only the processing of angle A1 is discussed for clarity. The leading edge pick off circuit block 92 establishes angle A1 from the threshold circuit block 90 output. This angle value is impressed upon a sine look-up table 96. The value of sine A1 is multiplied by the distance F1 in multiplier 98 to calculate the distance CR1. Angle A1 is also impressed upon a cosine look-up table 100. The value of cosine A1 is then multiplied by the distance CR1 in multiplier 102 to arrive at distance D1. Distance D1 and angle A1 are then used to calculate the polar coordinates of one point on the perimeter of the object. The elements 96–102 can be replaced by a single pre-calculated look-up table that could be calculated from the geometry or established by calibration measurements of known-size objects. The elements 90–102 can be implemented as analog circuitry, as digital hardware or can be implemented in software running on a programmable device. An analog-to-digital converter would be used to digitize the video signal in a digital implementation. Other sensors such as photo-diodes, phototransistors, avalanche photo-diodes, photo-resistive sensors, or other photo-electric sensors can also be used.

Determination of the map of the perimeter of the scanned object has several useful applications. The perimeter map is centered on the axis of rotation of the orbit around the scanned object. Since the location of the laser beam is known as a function of the perimeter at each position in the orbit of the scanned object, the optical path length from the point at which the laser beam impinges on the scanned object to each point on the perimeter is also known.

Figure 10:
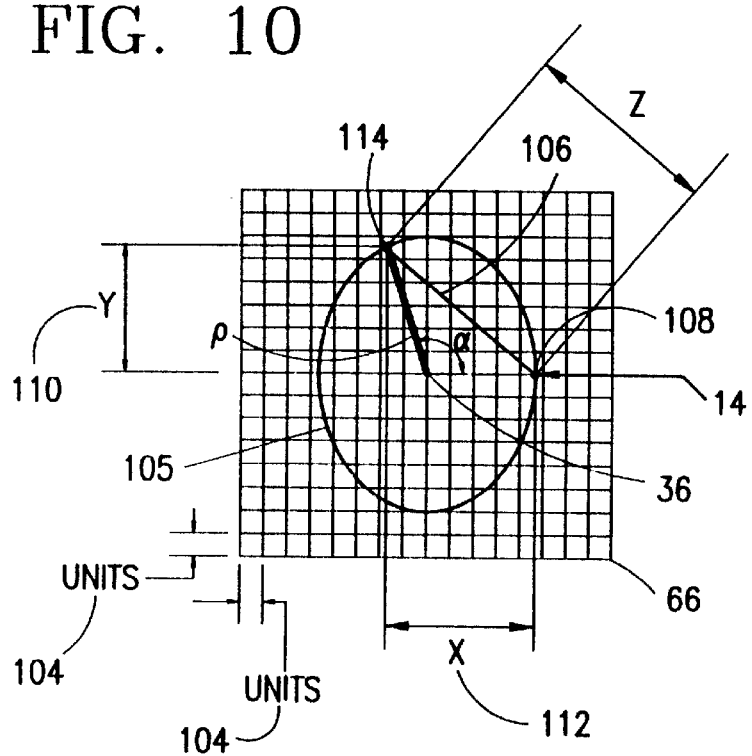
FIG. 10 shows a perimeter plot on a perimeter matrix, illustrating the determination of a path length of the impinging laser beam through the scanned object.

Referring to FIG. 10, the perimeter matrix 66 with units 104, is shown with a perimeter plot. The laser beam 14 impinges the scanned object at point 108 on the perimeter plot. A straight line optical path 106 is drawn through the object from the point 108 to a point 114 defined by the polar angle $\alpha$ and a polar radius $\rho$. The perimeter matrix 66 has its center aligned with the axis of rotation of the scanning chamber. After the perimeter matrix 66 is calibrated, the units 104 of the matrix are known. After the perimeter 105 of the scanned object is superimposed on the matrix 66, point 108 at which the laser beam 14 impinges on the surface of the scanned object can be located in the perimeter matrix. For each angle $\alpha$, the point at which the polar radius $\rho$ intersects the superimposed perimeter 64 of the scanned object can also be determined. The Y distance 110 is equal to D1 and can also be determined from the perimeter matrix 66. The X distance 112 can be determined from the perimeter matrix. The optical path 106, the distance Z through the scanned object can, therefore, be determined from the X and Y distances using the principle of right triangles in the following equation, $$\text{Distance } Z = \text{Square Root } (x^2 + y^2) \quad (7)$$

Other mathematical means could be used to determine the optical path 106.

Knowledge of the optical path length and the index of refraction of the material of the scanned object provides knowledge of the optical delay encountered by photons traveling within the scanned object. This optical delay parameter is useful in time-gated studies where only a portion of the photons emerging from the scanned object are desired as acquired data.

Knowledge of the optical path length also provides the means for adjusting parameters in a data acquisition method. For example, knowledge of the optical path length provides an indication of the optical attenuation through the scanned object. Knowledge of the optical attenuation could be used to control the power of the laser or gains of the detectors.

Because the knowledge of the perimeter of a scanned object is known for all positions of the orbit, an adaptive data acquisition scheme is possible and could be used to optimize data acquisition parameters.

Use of the perimeter data of the scanned object is discussed in provisional applications Ser. Nos. 60/032,590, 60/032,592, 60/032,594 and 60/032,593, all filed on Nov. 29, 1996, which are hereby incorporated by reference.

Figure 11:
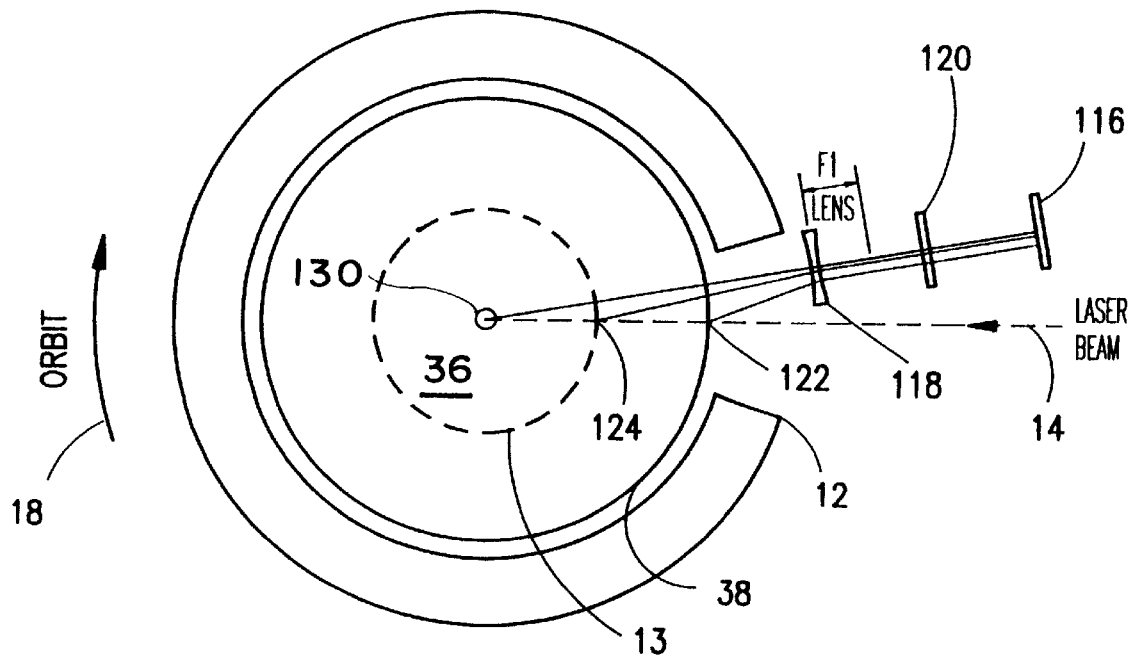
FIG. 11 is a schematic view of the scanning chamber of FIG. 1 using another embodiment of the present invention for determining the perimeter of the scanned object.

Another embodiment of the present invention is disclosed is FIG. 11. A sensor array 116, lens 118 and attenuation filter 120 are disposed on the same side as the laser beam 14. Calibration standards 13 and 38 are used to calibrate the perimeter matrix and the sensor array 116. It should be understood that the calibration standards 13 and 38 would be used one at a time, although they are shown together for ease of discussion. The laser beam 14 impinges on the scanned objects 38 and 13 through the center 36 of the orbit. Bright spots are produced at points 122 and 124. The attenuation filter 120 is used to reduce the intense brightness of the spots 122 and 124. At each diameter of the scanned objects 13 and 38, a specific element in the sensor array 116 will detect each of spots 122 and 124. The lens 118 is used to focus the light with greater precision on the sensor array 116.

Referring to FIG. 12, rays 126 and 128 are reflected from the spots 122 and 124, respectively, to illuminate different elements of the sensor array 116. Different diameters of the scanned object will selectively stimulate different sensor array elements. A pin 130 placed in the center 36 and an object of maximum size 38 can be used to calibrate the elements of the sensor array 116 that corresponds to the minimum and maximum diameters, respectively, in the path of the laser beam 14. As the laser beam 14, detector array 12, the sensor array 116, the lens 118 and the attenuation filter 120 are orbited around the scanned object about the center 36, the output signal of the sensor array 116 will be in direct relationship to the perimeter of the scanned object. By acquiring data using one or more known diameters scanned objects, the level of the sensor signal can be calibrated with respect to the scanned object diameters. After calibration, the sensor signal can be electronically decoded to plot the coordinates for the perimeter of the scanned object as the scanning chamber is orbited around the scanned object. Ray 132 would also hit a different element in the array 116, as best shown in FIG. 11.

An exemplary block diagram of a circuit for determining the perimeter location from the sensor signals generated at the sensor array 116 is disclosed in FIG. 13. The sensor array 116 is implemented with a ccd camera sensor 134, preferably a linear ccd array, whose video output is digitized by ADC(analog/digital converter) 136 into a digital video stream 138. The video plot will typically be a single peak (the laser beam impinging on the scanned object) on a relative flat field. The location of this peak is determined by a centroid calculation block 140. The peak's centroid location would be impressed on a look-up table 142 which would output a perimeter distance value, typically in polar coordinates from the rotation center. The position look-up table could either be established from the physical geometry or by calibration measurements of known size objects.

While this invention has been described as having preferred design, it is understood that it is capable of further modification, uses and/or adaptations following in general the principle of the invention and including such departures from the present disclosure as come within known or customary practice in the art to which the invention pertains, and as may be applied to the essential features set forth, and fall within the scope of the invention or the limits of the appended claims.

We claim:

1. An apparatus for determining the perimeter of an object being scanned, comprising:
   a) a scanning chamber for receiving therein an object being scanned;
   b) a laser beam disposed within said scanning chamber for impinging on the object being scanned, said laser beam for orbiting around the object;
   c) an array of sensors disposed within said chamber, each of said sensors for detecting light emanating from the surface of the object due to said laser beam impinging on the object;
   d) each of said sensors being disposed such that one of said sensors generates a peak response to light emanating from a point on the surface at a predetermined distance from a reference point, such that at each angular position of said laser beam in the orbit, a specific point at a distance from the reference is determined, thereby to generate a set of points representing the perimeter of the surface after a complete orbit.

2. An apparatus as in claim 1, and further comprising:
   a) a diverging lens disposed in front of said sensors.

3. An apparatus as in claim 1, wherein:
   a) said laser beam is directed through a axis of the orbit.

4. An apparatus as in claim 1, wherein:
   a) said sensors are disposed on the same side of the object being scanned as said source of laser beam.

5. An apparatus as in claim 4, wherein:
   a) said sensors are disposed such as to detect light reflected from a point on the surface at which said laser beam impinges the surface.

6. An apparatus as in claim 1, wherein:
   a) said sensors are CCD optical sensors.

7. An apparatus as in claim 1, wherein:
   a) said sensors include photodiodes.

8. An apparatus as in claim 1, wherein:
   a) said sensors include phototransistors.

9. An apparatus as in claim 1, wherein:
   a) said sensors include avalanche photodiodes.

10. An apparatus as in claim 1, wherein:
    a) said sensors include photoresistive sensors.

11. An apparatus as in claim 1, wherein:
    a) said sensors include photoelectric sensors.

12. An apparatus as in claim 1, wherein:
    a) said sensors are disposed opposite said laser beam across the object being scanned.

13. An apparatus as in claim 12, wherein:
    a) said sensors are disposed to detect light along a tangent line to a point on the surface and a point behind said sensors.

14. An apparatus as in claim 12, wherein:
    a) said sensors are disposed opposite said laser beam on a line through a center of the orbit.

15. An apparatus as in claim 14, wherein:
    a) said sensors are disposed on a linear array; and
    b) said array is disposed transversely to said line through the center of the orbit.

16. A method for determining the perimeter of an object being scanned, comprising:
    a) providing a laser beam;
    b) directing the laser beam toward the object being scanned;
    c) orbiting the laser beam around the object;
    d) providing a plurality of sensors for detecting light emanating from the surface due to the laser beam impinging on the object;
    e) detecting at each angular position of the orbit light emanating from the surface of the object at a unique one of the sensors for each point on the surface at a predetermined specific distance from a reference point such that a collection of points from the surface are generated during a complete orbit of the laser beam;
    f) determining the perimeter of the object from the collection of points.

17. A method as in claim 16, and further comprising the step of:
    a) positioning the sensors on the same side of the object being scanned as the laser beam.

18. A method as in claim 16, and further comprising the step of:
    a) positioning the sensors opposite the laser beam across the other side of the object being scanned.

19. An apparatus for determining the perimeter of an object being scanned, comprising:
    a) a scanning chamber for receiving therein an object being scanned;
    b) a laser beam disposed within said scanning chamber for impinging on the object being scanned, said laser beam for orbiting around the object;
    c) a linear array of sensors disposed within said chamber, each of said sensors for detecting light reflecting from the surface of the object due to said laser beam impinging on the object; and
    d) each of said sensors being disposed such that one of said sensors generates a peak response to light emanating from a point on the surface at a predetermined distance from a reference point, such that at each angular position of said laser beam in the orbit, a specific point at a distance from the reference is determined, thereby to generate a set of points representing the perimeter of the surface after a complete orbit.

* * * * *